(12) United States Patent
Iwabuchi et al.

(10) Patent No.: US 7,278,330 B2
(45) Date of Patent: Oct. 9, 2007

(54) METHOD OF INSPECTING POROUS STRUCTURE

(75) Inventors: Muneyuki Iwabuchi, Nagoya (JP); Shinya Mori, Nagoya (JP); Shuuji Ueda, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 280 days.

(21) Appl. No.: 11/082,873

(22) Filed: Mar. 18, 2005

(65) Prior Publication Data

US 2005/0217395 A1    Oct. 6, 2005

(30) Foreign Application Priority Data

Mar. 31, 2004    (JP)    ............... 2004-107442

(51) Int. Cl.
*G01N 33/00*    (2006.01)
(52) U.S. Cl. ..................................... 73/866
(58) Field of Classification Search ............ 73/38, 73/866, 865.8
See application file for complete search history.

(56) References Cited

FOREIGN PATENT DOCUMENTS

| JP | A 09-120067 | 5/1997 |
|----|-------------|--------|
| JP | A 2002-219319 | 8/2002 |

*Primary Examiner*—Robert Raevis
(74) *Attorney, Agent, or Firm*—Oliff & Berridge, PLC

(57) ABSTRACT le;2qThere is disclosed a method of inspecting a porous structure, capable of simply inspecting pore characteristics (porosity, average pore diameter, total pore volume) of the porous structure by inspection of a weight of a formed article which was formed, dried and worked into a predetermined dimension without requiring any special device or technique, and capable of easily performing a total inspection. A relation between a pore characteristics of a fired article obtained by firing a formed/dried formed article having a predetermined shape, and a weight of the formed article is measured beforehand, and a standard value of the pore characteristics of the fired article, and a standard value of the weight of the formed article are established. Thereafter, the pore characteristics of the fired article are inspected from the weight of the formed article based on the respective standard values.

11 Claims, 4 Drawing Sheets

METHOD OF INSPECTING POROUS STRUCTURE

BACKGROUND OF THE INVENTION

1. Field of the Invention

The present invention relates to a method of inspecting a porous structure.

2. Description of the Related Art

A ceramic honeycomb structure has been widely used as a dust collecting filter for use in applications such as a pollution preventing environment countermeasure and product recovery from a high-temperature gas in various fields including chemical plants, electric power plants, iron and steel works, and disposal for industrial waste since it has a superior heat resistance and corrosion resistance. For example, a diesel particulate filter (DPF) for capturing particulates discharged from a diesel engine and the like are used under severe conditions such as high temperature and corrosive gas atmosphere, and therefore a ceramic honeycomb structure has been preferably used.

Especially in recent years, from a necessity of enhancing process capability of a dust collecting filter, there has been a demand for a ceramic honeycomb structure having a low pressure loss and a high porosity, and having required levels of an average pore diameter and pore volume in accordance with a dust collection performance as well. As a method of manufacturing a ceramic honeycomb structure (porous honeycomb structure) having a high porosity, a method of manufacturing a porous honeycomb filter has been proposed in which a mixture of a binder (organic binder such as methyl cellulose), a pore forming agent (organic material such as graphite) and the like, in addition to aggregate particle materials such as cordierite forming material and water, are kneaded to form a plastic material having plasticity, and the resultant is dried, and fired (see JP-A-2002-219319).

Moreover, a ceramic filter has been used in order to remove bacteria and particulates of waste contained in sewage for purification. For example, a ceramic porous article is preferably used in a final step for purifying drinking water in a water purification plant. Thus, there has been a demand for a ceramic filter having a high porosity, and the required levels of an average pore diameter and pore volume in accordance with filtering capability in order to enhance a filtering amount even in the purification of the drinking water.

Usually, the pore characteristics of a formed article obtained by extrusion are inspected to assure that a porous structure as a product can satisfy the predetermined levels of the characteristics as to pore (the characteristics as to pore is hereinafter referred to as pore characteristics) inclusive of the porosity, the average pore diameter, the total pore volume and the like of the porous structures produced. In the inspection, sampling inspection has been mainly performed by using measurement methods such as an Archimedes process and mercury press-in porosimeter.

However, in the case of the produced structures obtained by the extrusion, in the sampling inspection, there remains a possibility that the products having defects in the pore characteristics are sent to the users or the next step. For example, in a case where sudden troubles such as changes in subtle forming conditions occur during the extrusion, such as for example, unusual operation state of a kneader, there has been a problem that the products having defects are sent at a relatively high probability to the users or the next step.

Moreover, since the measurement methods using Archimedes process and the mercury press-in porosimeter require not only special devices and techniques but also the laborious procedures and costs, it has been actually difficult to carry out a total inspection.

Furthermore, after the sampling inspection, both end faces of the formed article should be alternately plugged in a checkered pattern flag-like manner. Thus, the plugging is performed in vein as far as the porous structures having defects overlooked due to the sampling inspection are concerned. This has caused cost increases.

SUMMARY OF THE INVENTION

The present invention has been developed in view of the above-described conventional technical problems, and an object thereof is to provide a method of inspecting a porous structure, capable of simply inspecting pore characteristics inclusive of porosity, average pore diameter, total pore volume of the porous structure by inspection of a weight of a formed article which was extruded, dried and worked into a predetermined dimension without requiring any special device or technique, and capable of easily performing a total inspection during the production and/or after the production.

Therefore, the present invention is to provide a method of inspecting a porous structure to achieve the above-described objects.

[1] A method of inspecting a porous structure which comprises the steps of: measuring beforehand a relation between pore characteristics of a fired article obtained by firing a dried formed article having a predetermined shape, and a weight of the formed article by using a predetermined number of formed articles and fired articles; establishing a standard value of the pore characteristics of the fired article, and a standard value of the weight of the formed article based on thus obtained relations; and determining the pore characteristics of the fired article from the weight of the formed article based on the respective standard values.

[2] The method of inspecting the porous structure according to [1], wherein the inspection is carried out based on a working curve showing a relation between the pore characteristics of the fired article, and the weight of the formed article, or the standard values calculated using an approximate equation or established values; said working curve, said approximate equation and said established values having been prepared prior to the inspection.

[3] The method of inspecting the porous structure according to [1] or [2], which further comprises the steps of: measuring the weights of a specified number of the formed articles prior to measurement of all products to thereby calculate an average value of the weights; and giving an upper-limit threshold value and a lower-limit threshold value to the standard value of the weight of the formed article based on the average value of the weight.

[4] The method of inspecting the porous structure according to any one of [1] to [3], wherein the standard value of the pore characteristics of the fired article is defined by the upper-limit threshold value and the lower-limit threshold value of porosity of the fired article.

[5] The method of inspecting the porous structure according to any one of [1] to [4], wherein the standard value of the pore characteristics of the fired article is defined by the upper-limit threshold value and the lower-limit threshold value of pore diameter of the fired article.

[6] The method of inspecting the porous structure according to any one of [1] to [5], wherein the standard value of the pore characteristics of the fired article is defined by the upper-limit threshold value and the lower-limit threshold value of pore volume of the fired article.

[7] The method of inspecting the porous structure according to any one of [1] to [6], further comprising the steps of: preparing the working curve or the approximate equation every time when a size or a lot of the formed article or the fired article is changed.

[8] The method of inspecting the porous structure according to any one of [1] to [7], wherein the porous structure is a porous honeycomb structure.

In the method of inspecting the porous structure according to the present invention, the pore characteristics inclusive of porosity, average pore diameter, total pore volume and the like of the formed article which was formed, dried and worked into the predetermined dimension can be simply performed by the inspection of the weight of the formed article which was formed, dried and worked into the predetermined dimension without requiring any special device or technique, and the total inspection can also be performed easily.

DESCRIPTION OF THE PREFERRED EMBODIMENT

Figure 1:
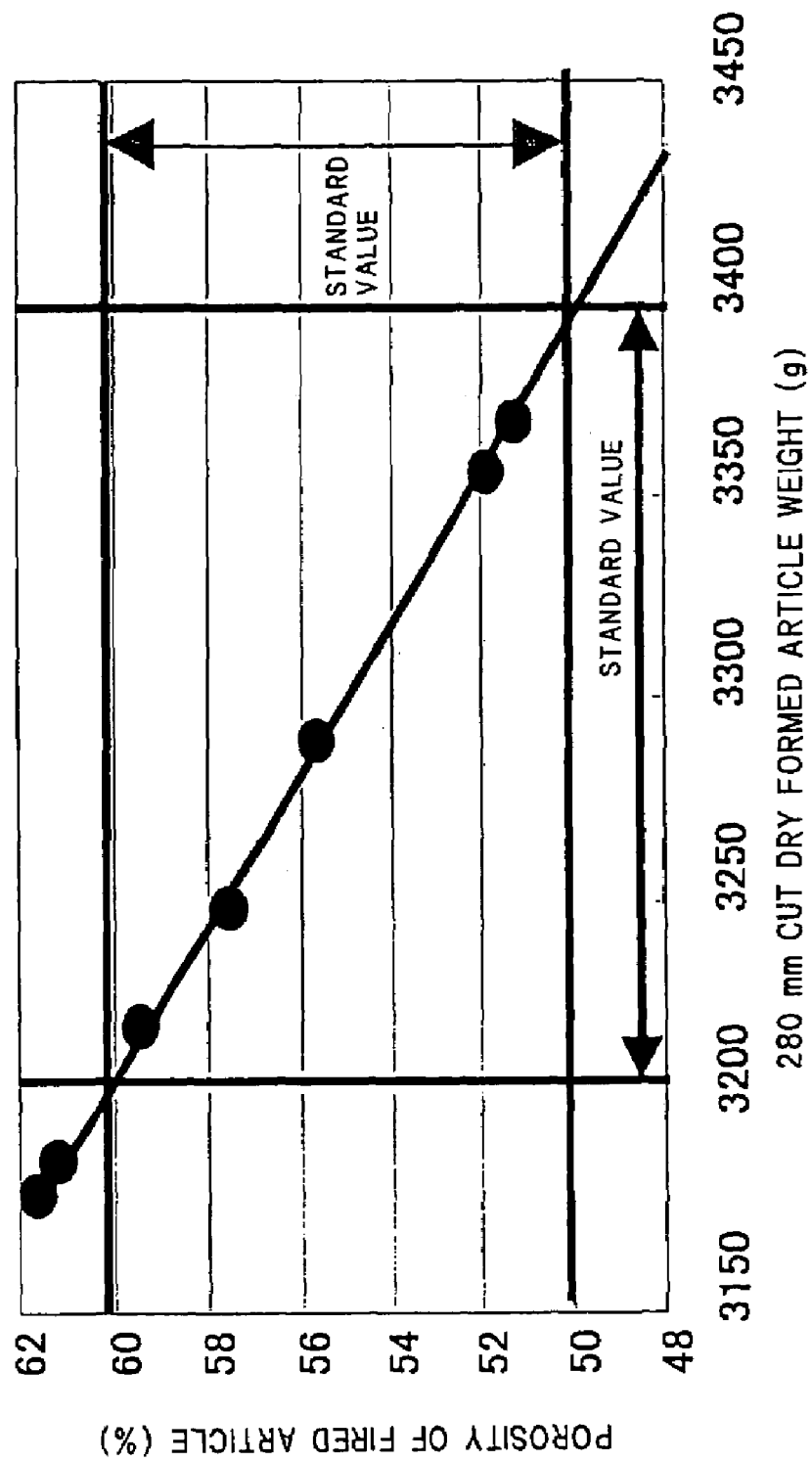
FIG. 1 is a graph showing a relation between porosity of a fired article of a porous honeycomb structure (formed article) and dry weight change ratio of the formed article cut into a length of 280 mm, and a working curve and standard value of the porous honeycomb structure (formed article)

An embodiment of a method of inspecting a porous structure according to the present invention will be described hereinafter in detail, but the present invention is not limited to this and interpreted as such, and can be variously changed, modified, and improved based on knowledge of a person skilled in the art without departing from the scope of the present invention.

Main characteristics of the method of inspecting the porous structure of the present invention lie in that a relation between pore characteristics of a fired article obtained by firing a formed article which was formed, dried and worked into a predetermined dimension, and a weight of the formed article, and a standard value of the pore characteristics of the fired article, and a standard value of the weight of the formed article are established by using a predetermined number of the actual production products during and/or after the manufacturing of the porous structure. Thereafter, the pore characteristics of the fired article can be inspected from the weight of the formed article based on the respective standard values.

Consequently, the present invention does not require measurement methods such as an Archimedes process and mercury press-in porosimeter performed in inspecting a pore characteristics including porosity, an average pore diameter, a total pore volume and the like of a fired article, the inspection requiring a special device or technique. The laborious procedures and costs required therefor are largely reduced. The pore characteristics inclusive of porosity, average pore diameter, and total pore volume of a fired article can be simply confirmed, when a total inspection of weights of formed articles which were formed, dried and worked into predetermined dimensions is performed. Therefore, even occurrence of sudden troubles during the production can be quickly managed, and defectives can be momentarily distinguished. Therefore, the defectives can be prevented from being passed to a next firing or another step, and this can contribute to enhancement of yield.

Next, a process of the method of inspecting the porous structure of the present invention will be described.

(1) First, a relation between a porosity, pore diameter, and pore volume of a fired article obtained by firing a formed article which was formed, dried and worked into a predetermined dimension, and a weight of the formed article is measured, and a working curve or an approximate equation is prepared beforehand. For example, the working curve based on weight data of the formed article is prepared from weight data of the formed article measured beforehand, and data of the porosity, pore diameter, and pore volume ratio of the fired article at the time when the formed article is fired (see FIGS. 1 to 3).

The weights of the formed articles are measured before measuring all products to thereby calculate an average value of the weights, and an upper-limit threshold value and a lower-limit threshold value are given to the standard value of the weight of the formed article based on the average value. It is to be noted that the threshold value in the standard value of the weight of the formed article is established by pore characteristic required for a fired article.

(2) The standard values of the porosity, pore diameter, and pore volume ratio of the fired article can be calculated from each working curve (see FIGS. 1 to 3) based on the standard value of the weight of the formed article.

(3) For example, in an actual manufacturing step (extrusion step), the weight of the formed article which was formed, dried and worked into the predetermined dimension is simply measured based on the working curve obtained in (1) and the standard values of the porosity, pore diameter, and pore volume ratio of the fired article. Then, the porosity, pore diameter, and pore volume ratio of the fired article are inspected, and non-defectives and defectives of the formed articles are sorted.

Here, weights of several to several tens of formed articles are measured before measuring all the products to thereby calculate an average value, and an upper-limit threshold value and lower-limit threshold value are given to the standard value of the weight of the formed article based on the average value. As to widths of the upper and lower-limit threshold values, an allowable range of +3% is preferably given to the average value. As to the average value, for example, when a target of the porosity is established to 50% article (measured weight 3399 g) to 60% article (measured weight 3201 g), an average weight (3300 g)+3% is established as a fluctuation width of an average 55% article. At this time, the pore diameter and pore volume are measured, and the standard value of the weight of the final formed article is preferably established from the widths of the upper and lower-limit threshold values of the targeted porosity, pore diameter, and pore volume.

Moreover, in the method of inspecting the porous structure of the present invention, the tolerance range of a reference value is preferably defined by the upper and lower-limit threshold values of the porosity, pore diameter, and pore volume of the fired article. It is to be noted that the porous structure is further preferably a porous honeycomb structure.

Furthermore, in the method of inspecting the porous structure according to the present invention, the working curve or the approximate equation is preferably prepared every time when a size or a lot of the formed article or the fired article is changed. Here, the term "lot" means a predetermined number of articles, for example, several to several tens of thousands of articles every forming material blend, every forming day, every drying day, and every firing, or for several blends, and several days.

EXAMPLES

The present invention will be described in more detail in accordance with examples of a porous honeycomb structure, but the present invention is not limited to the examples.

EXAMPLE

A porous honeycomb structure (formed article) having a porosity of 50 to 60% ($\phi$200 mm×280 mmL, partition wall thickness of 1.5 mm, cell density of 15 cells/cm$^2$, outer peripheral wall thickness of 2 mm) was extruded from a kneader via a ferrule. Seven formed articles cut into each length of 280 mm and having different dry weights (dry formed articles) were prepared. Next, porosities, pore diameters, and pore volumes were measured from seven fired articles. Next, working curves each showing a relation between the dry formed article weight and the porosity, pore diameter, and pore volume of the fired article were prepared from the obtained data (see FIGS. 1 to 3). To prepare the working curve, the number of fired articles is preferably large, and 2 to 50, preferably 3 to 10 articles may be used.

Figure 2:
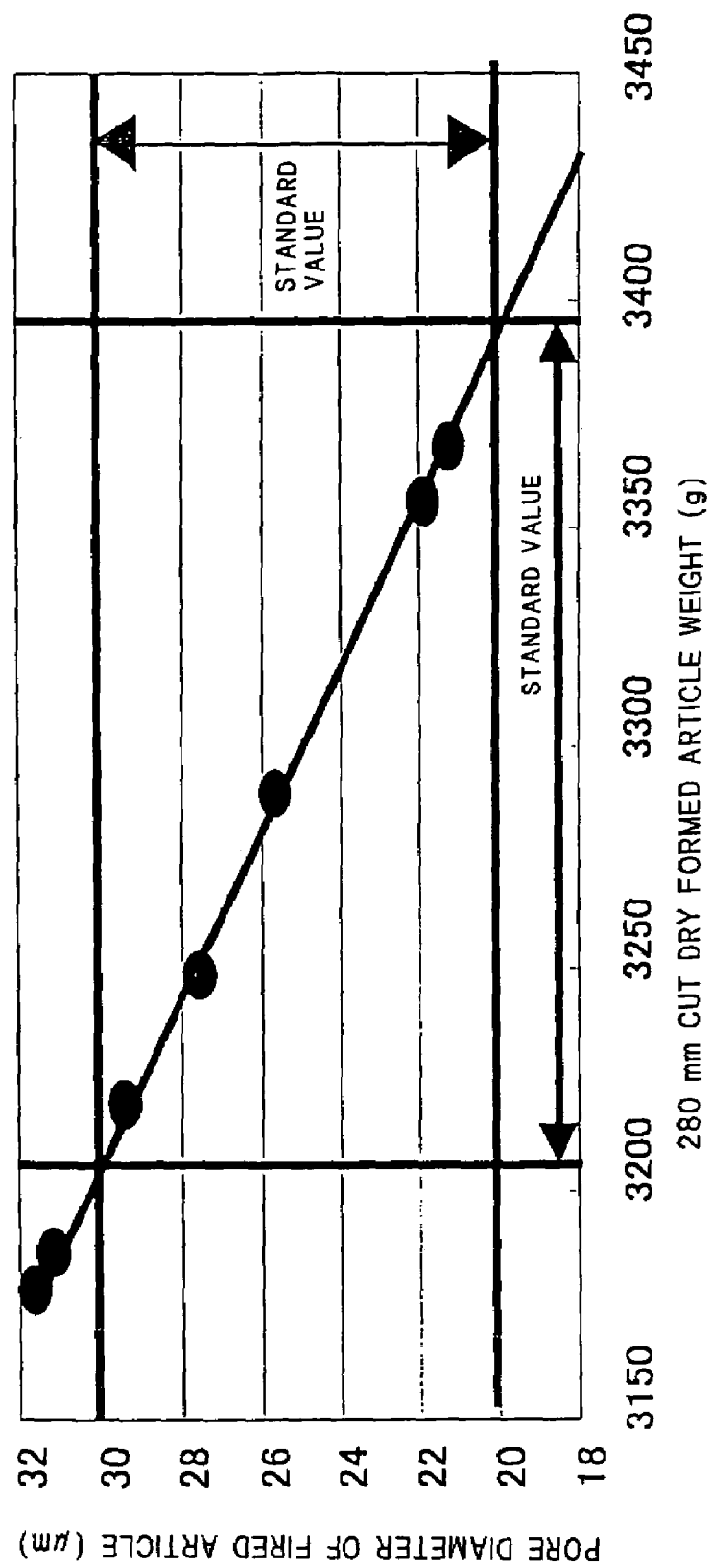
FIG. 2 is a graph showing a relation between a pore diameter of the fired article of the porous honeycomb structure (formed article) and dry weight change ratio of the formed article cut into a length of 280 mm, and a working curve and standard value of the porous honeycomb structure (formed article)
Figure 3:
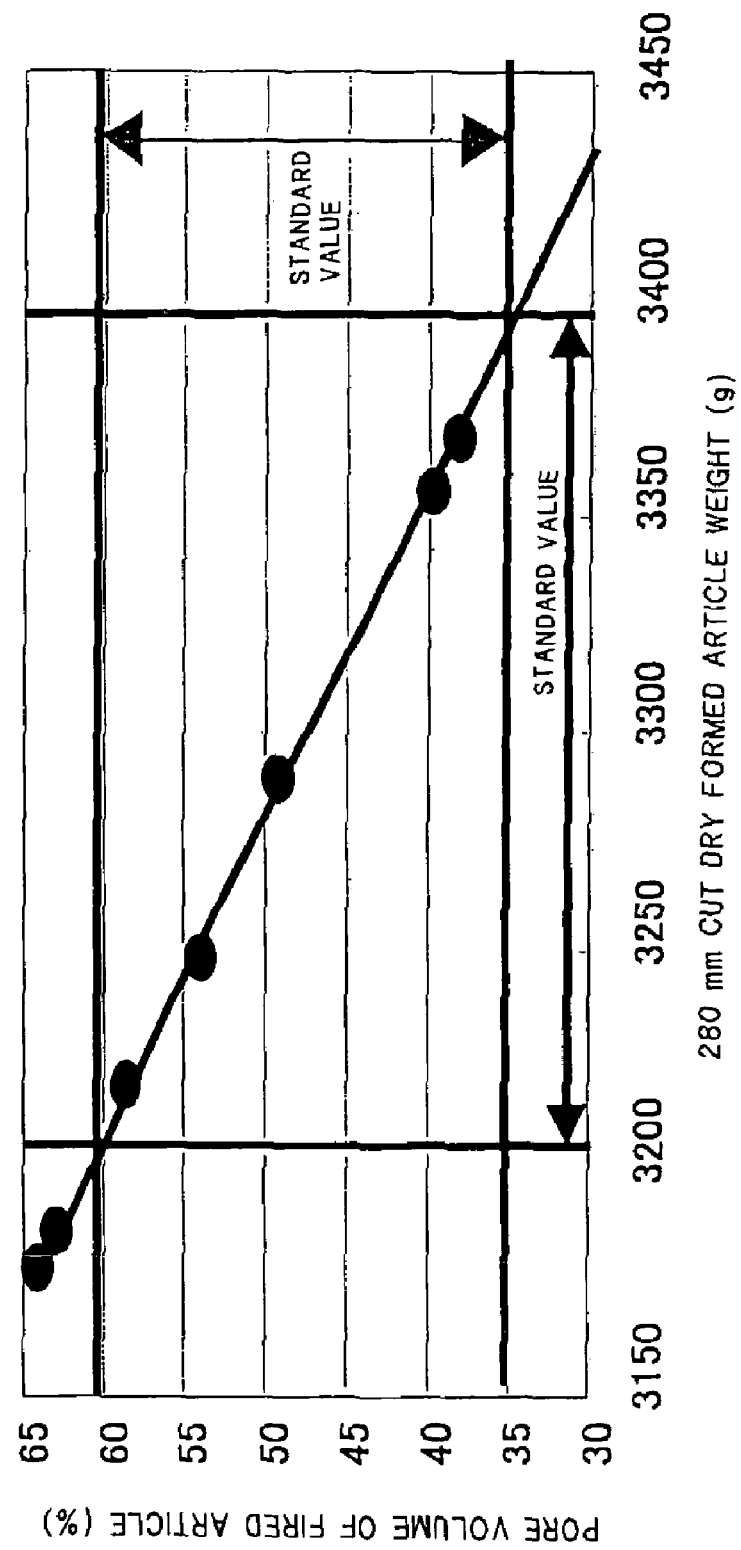
FIG. 3 is a graph showing a relation between pore volume of a fired article of a porous honeycomb structure (formed article) and dry weight change ratio of the formed article cut into a length of 280 mm, and a working curve and standard value of the porous honeycomb structure (formed article)

From the obtained working curves shown in FIGS. 1 to 3, a standard value of the weight of the formed article was established to 3300+99 g, a standard value of the porosity of the fired article was established to 50 to 60%, a standard value of the pore diameter of the fired article was established to 20 to 30 $\mu$m, and a standard value of the pore volume of the fired article was established to 35 to 60%.

Figure 4:
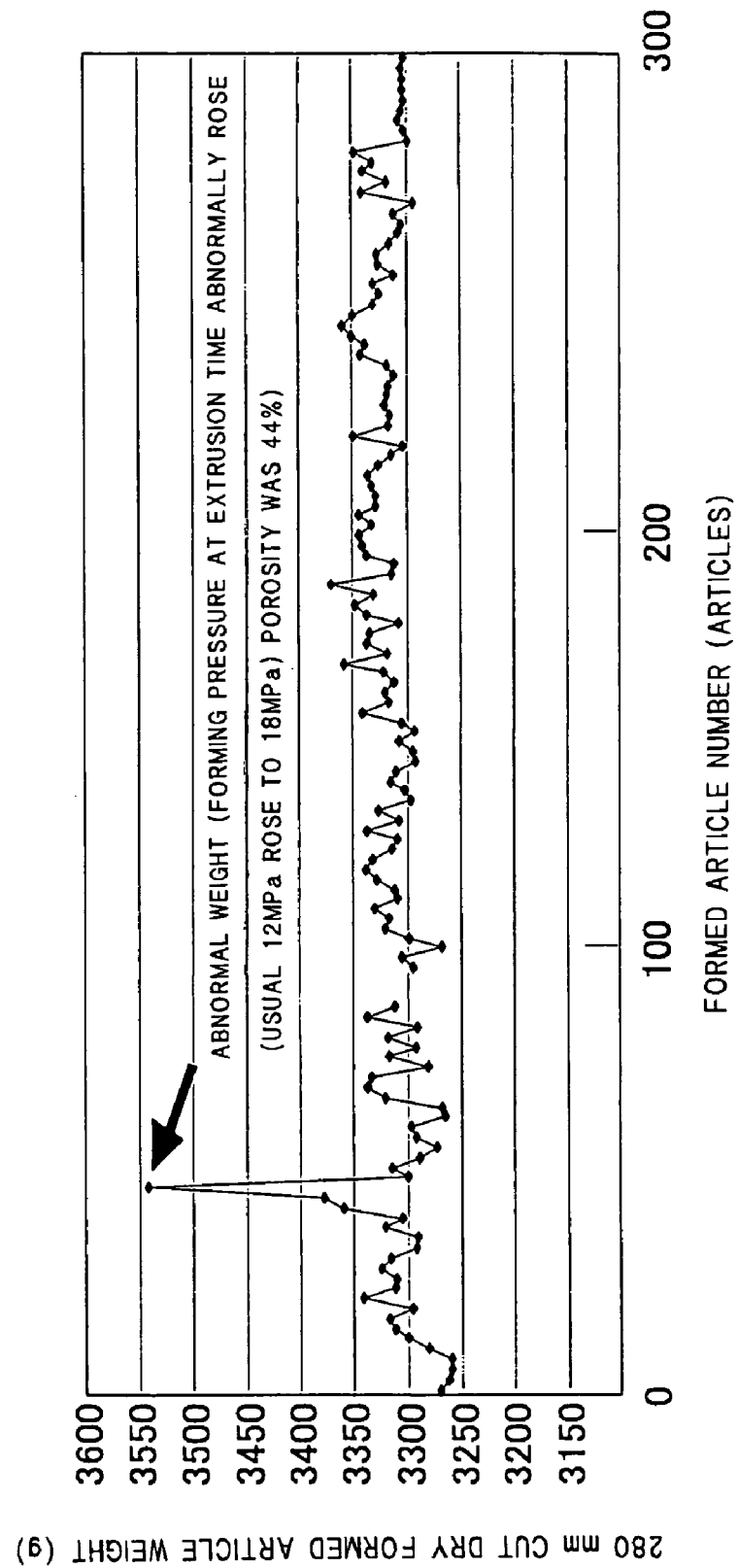
FIG. 4 is an explanatory view of an application example (porous honeycomb structure) in a method of inspecting a porous structure of the present invention.

Next, the extrusion was performed in the same manner as described above, taking into the respective obtained standard values consideration, then a total inspection (500 articles) of the porosities of the fired articles was performed by measuring the weight of each fired article to sort non-defectives/defectives. One example of the results of such inspections is shown in FIG. 4.

Comparative Example

After firing a porous honeycomb structure similar to that of the example, three articles were appropriately sampled from 500 fired articles to inspect the presence of the defectives. At this time, a mercury press-in porosimeter was used in measuring the porosity, pore diameter, and pore volume.

Conclusion

In the examples, 2.4% of the articles produced were found to be the ones deviating from a dry weight standard of the formed article cut into a length of 280 mm, while this lot was judged to pass the inspection in case of the sampling inspection of the Comparative Example since the porosity of the fired article was within the established value in the sampling inspection. In actual, 2.4% of the articles having defects in the porosity, pore diameter, and pore volume defectives was included in the passed lot. As a result of confirmation of the porosity, pore diameter, and pore volume of each fired article obtained by firing the formed article cut into a length of 280 mm and deviating from the dry weight standard, a porosity less than 50%, pore diameter less than 20 $\mu$m, and pore volume less than 35% deviated from standard values. In the present invention, by measurement of dry weights of a total number of formed articles cut into each length of 280 mm, a total number of porosity, pore diameter, and pore volume defectives, which had not been detected in the Comparative Example, were removed. In the present invention, even when sudden troubles would occur at a forming time of a honeycomb structure, non-defectives/defectives could be securely and easily selected.

In the Comparative Example, the found ratio of the defectives in either porosity, pore diameter, or pore volume was about 1%. However, since a mercury press-in porosimeter was used, much labor was required in inspection. Therefore, it is impossible to select sort out properly the non-defectives/defectives when sudden troubles occur.

The method of inspecting the porous structure of the present invention can be preferably used in the total inspection of the pore characteristics (porosity, pore diameter, and pore volume) of the porous structure.

What is claimed is:

1. A method of inspecting a honeycomb structure which comprises the steps of:

obtaining a relation between a pore characteristic of a fired honeycomb structure and a weight of a formed honeycomb structure, the fired honeycomb structure being obtained by firing the formed honeycomb structure, the formed honeycomb structure having a predetermined shape and being dried, the relation being obtained by using measurements of a predetermined number of formed honeycomb structures and fired honeycomb structures;

establishing a standard value of the pore characteristic of the fired honeycomb structure, and a standard value of the weight of the formed honeycomb structure based on the obtained relation and predetermined requirements for the pore characteristic; and inspecting the pore characteristics of the fired honeycomb structure from the weight of the formed honeycomb structure based on the respective standard values.

2. The method of inspecting the honeycomb structure according to claim 1, wherein the inspection is carried out based on a working curve showing the relation between the pore characteristic of the fired honeycomb structure, and the weight of the formed honeycomb structure, or the standard values calculated using an approximate equation or established values; said working curve, said approximate equation and said established values having been prepared prior to the inspection.

3. The method of inspecting the honeycomb structure according to claim 2, which further comprises the steps of:

measuring weights of the predetermined number of the formed honeycomb structures prior to obtaining the relation to thereby calculate an average value of the weights; and providing an upper-limit threshold value and a lower-limit threshold value to the standard value of the weight of the formed honeycomb structure based on the average value.

4. The method of inspecting the honeycomb structure according to claim 2, wherein the standard value of the pore characteristic of the fired honeycomb structure is defined by an upper-limit threshold value and a lower-limit threshold value of porosity of the fired honeycomb structure.

5. The method of inspecting the honeycomb structure according to claim 2, wherein the standard value of the pore characteristic of the fired honeycomb structure is defined by an upper-limit threshold value and a lower-limit threshold value of a pore diameter of the fired honeycomb structure.

6. The method of inspecting the honeycomb structure according to claim 2, wherein the standard value of the pore characteristic of the fired honeycomb structure is defined by an upper-limit threshold value and a lower-limit threshold value of a pore volume of the fired honeycomb structure.

7. The method of inspecting the honeycomb structure according to claim 2, further comprising the steps of: preparing the working curve or the approximate equation every time when a size or a lot of the formed honeycomb structure or the fired honeycomb structure is changed.

8. The method of inspecting the honeycomb structure according to claim 1, which further comprises the steps of:

measuring weights of the predetermined number of the formed honeycomb structures prior to obtaining the relation to thereby calculate an average value of the weights; and providing an upper-limit threshold value and a lower-limit threshold value to the standard value of the weight of the formed honeycomb structure based on the average value.

9. The method of inspecting the honeycomb structure according to claim 1, wherein the standard value of the pore characteristic of the fired honeycomb structure is defined by an upper-limit threshold value and a lower-limit threshold value of porosity of the fired honeycomb structure.

10. The method of inspecting the honeycomb structure according to claim 1, wherein the standard value of the pore characteristic of the fired honeycomb structure is defined by an upper-limit threshold value and the lower-limit threshold value of a pore diameter of the fired honeycomb structure.

11. The method of inspecting the honeycomb structure according to claim 1, wherein the standard value of the pore characteristic of the fired honeycomb structure is defined by an upper-limit threshold value and a lower-limit threshold value of a pore volume of the fired honeycomb structure.

* * * * *